(12) United States Patent
Smith et al.

(10) Patent No.: US 7,532,317 B2
(45) Date of Patent: May 12, 2009

(54) SCATTEROMETRY METHOD WITH CHARACTERISTIC SIGNATURES MATCHING

(75) Inventors: Nigel Smith, Hsinchu (TW); Yi-sha Ku, Hsinchu (TW); Shih Chun Wang, Taipei (TW); Chun-hung Ko, Taipei (TW)

(73) Assignees: Industrial Technology Research Institute, Taipei (TW); Nanometrics Incorporated, Milpitas, CA (US)

( * ) Notice: Subject to any disclaimer, the term of this patent is extended or adjusted under 35 U.S.C. 154(b) by 360 days.

(21) Appl. No.: 11/319,677

(22) Filed: Dec. 28, 2005

(65) Prior Publication Data

US 2006/0146347 A1 Jul. 6, 2006

(30) Foreign Application Priority Data

Dec. 30, 2004 (TW) .............................. 93141298 A

(51) Int. Cl.
  *G01B 15/08* (2006.01)
(52) U.S. Cl. .......................... 356/237.2; 356/601; 703/4
(58) Field of Classification Search ... 356/237.2–237.6, 356/601–625, 630
  See application file for complete search history.

(56) References Cited

U.S. PATENT DOCUMENTS

| | | | |
|---|---|---|---|
| 6,515,745 B2 * | 2/2003 | Vurens et al. ................ | 356/369 |
| 6,657,736 B1 * | 12/2003 | Finarov et al. .............. | 356/625 |
| 6,768,967 B2 * | 7/2004 | Johnson et al. ............. | 702/179 |
| 6,785,638 B2 | 8/2004 | Niu et al. | |
| 6,842,261 B2 * | 1/2005 | Bao et al. ................... | 356/636 |
| 6,900,892 B2 * | 5/2005 | Shchegrov et al. .......... | 356/369 |
| 7,292,335 B2 * | 11/2007 | Brill et al. ................... | 356/319 |
| 2002/0035455 A1 * | 3/2002 | Niu et al. ...................... | 703/4 |

\* cited by examiner

*Primary Examiner*—L. G Lauchman
*Assistant Examiner*—Rebecca C Slomski
(74) *Attorney, Agent, or Firm*—Silicon Valley Patent Group LLP

(57) ABSTRACT

A system and method for efficiently and accurately determining grating profiles uses characteristic signature matching in a discrepancy enhanced library generation process. Using light scattering theory, a series of scattering signatures vs. scattering angles or wavelengths are generated based on the designed grating parameters, for example. CD, thickness and Line:Space ratio. This method selects characteristic portions of the signatures wherever their discrepancy exceeds the pre-set criteria and reforms a characteristic signature library for quick and accurate matching. A rigorous coupled wave theory can be used to generate a diffraction library including a plurality of simulated diffraction spectrums based on a predetermined structural parameter of the grating. The characteristic region of the plurality of simulated diffraction spectrums is determined based on if the root mean square error of the plurality of simulated diffraction spectrums is larger than a noise level of a measuring machine. The diffraction intensity of the measured diffraction spectrum is compared with that of the plurality of simulated diffraction spectrums in the characteristic region to select a match spectrum from these simulated diffraction spectrums, and the structural parameter of the grating is decided based on the match spectrum.

24 Claims, 11 Drawing Sheets

SCATTEROMETRY METHOD WITH CHARACTERISTIC SIGNATURES MATCHING

PRIORITY CLAIM

This application claims priority to Taiwan Patent Application No. 93141298, filed Dec. 30, 2004, which is hereby incorporated by reference.

BACKGROUND

The field of the invention is manufacturing semiconductor and similar micro-scale devices. More specifically, the invention related to scatterometry, which is a technique for measuring micro-scale features, based on the detection and analysis of light scattered from the surface. Generally, scatterometry involves collecting the intensity of light scattered or diffracted by a periodic feature, such as a grating structure as a function of incident light wavelength or angle. The collected signal is called a signature, since its detailed behavior is uniquely related to the physical and optical parameters of the structure grating.

Scatterometry is commonly used in photolithographic manufacture of semiconductor devices, especially in overlay measurement, which is a measure of the alignment of the layers which are used to form the devices. Accurate measurement and control of alignment of such layers is important in maintaining a high level of manufacturing efficiency.

Scatterometry measurements are made by finding the closest fit between an experimentally obtained signature and one obtained by other means and for which the value of the property or properties to be measured are known. Commonly, the second known signature, also known as the reference signature, is calculated from a rigorous model of the scattering process. It may occasionally be determined experimentally. Where a modeled signature is used as the reference, either the calculations are performed once and all signatures possible for the parameters of the grating that may vary are stored in a library, or the signature is calculated when needed for test values of the measured parameters.

However the reference signature is obtained, a comparison of the experimental and reference signature is made. The comparison is quantified by a value which indicates how closely the two signatures match. Commonly, the fit quality is calculated as the root-mean-square difference (or error) (RMSE) between the two signatures, but other comparison methods may be used. The measurement is made by finding the reference signal with the best value of fit quality to the experimental signature. The measurement result is then the parameter set used to calculate the reference signal. In the case of experimentally derived reference signatures, the reference signal is the value of the known parameters used to generate the experimental signature. As with any real system, the experimental signature obtained from the metrology system will contain some noise. This creates a lower limit to the fit quality that can be expected.

Microelectronic devices and feature sizes continue to get ever smaller. The requirement for the precision of overlay measurement of 130 nm node is 3.5 nm, and that of 90 nm node is 3.2 nm. For the next-generation semiconductor manufacturing process of 65 nm node, the requirement for the precision of overlay measurement is 2.3 nm. Since scatterometry has good repeatability and reproducibility, it would be advantageous to be able to use it in the next generation process. However, conventional bright-field metrology systems are limited by the image resolution. Consequently, these factors create significant technological challenges to the use of scatterometry with increasingly smaller features.

Conventional methods compare diffraction spectrums of unknown measurement with simulated diffraction spectrums. Methods such as the Levenberg Marquardt optimization, random search and genetic algorithm, compare the measured diffraction spectrum with an on-line generated simulated diffraction spectrum. This method is slow but can be used to measure a fully unknown grating. Other conventional methods such as principal component regression (PCR), partial least square (PLS), inverse least square (ILS) and artificial neural network (ANN), build a diffraction library in advance, and the measured diffraction spectrum is compared with the diffraction spectrums in the library to find a closest fit spectrum. This method can increase the processing speed, but needs more computer storage capacity than the first method. Methods such as described in U.S. Pat. No. 6,785,638 and U.S. Pat. No. 6,768,967, integrate both of these methods to increase the processing speed and decrease the storage capacity, but the algorithm used is much more complicated.

Conventional methods use static equations such as root mean square error (RMSE), mean square error (MSE) and square distance (SD) to compare the measured diffraction spectrum with the simulated diffraction spectrum entirely. However, RMSE or MSE average the entire diffraction spectrum, which leads to a region with a smaller variation, decreasing the entire comparison performance. Further, SD does not average the variation of variable as RMSE or MSE does, but it is much more sensitive to noise.

DETAILED DESCRIPTION OF THE INVENTION

Methods for deciding a structural parameter of a grating compare the similarity between a measured diffraction spectrum and a plurality of simulated diffraction spectrums in a characteristic region.

The method may include the steps of using a rigorous coupled wave theory to build a diffraction library including a plurality of simulated diffraction spectrums based on a predetermined structural parameter; selecting a characteristic region of the plurality of simulated diffraction spectrums on condition that the root mean square error of these simulated diffraction spectrums is larger than the noise level of a measuring machine; comparing the diffraction intensity of a measured diffraction spectrum from the grating and the diffraction intensity of the plurality of simulated diffraction spectrums in the characteristic region to find a match spectrum; and deciding the structural parameter of the grating based on the match spectrum.

Conventional angular scatterometry methods compare the entire diffraction spectrum between 0 and 47 degrees. This requires a large amount of computer memory and is time-consuming. In contrast, the present methods compare only a portion of the measured diffraction spectrum with the corresponding portion of these simulated diffraction spectrums in the characteristic region. This increases the processing efficiency and also decreases the computer memory requirements. Further, conventional methods average the entire diffraction spectrum average, which leads to a region with a smaller variation and decreases the entire comparison performance. In the present method, however, only a portion of the measured diffraction spectrum is compared with the corresponding portion of the simulated diffraction spectrums in the characteristic region. Averaging calculations are therefore avoided and measurement performance is improved.

The present methods can also be applied to determine structural parameters such as overlay error, line width, pitch, material parameters and thickness. Further, the present methods may also be applied to determine a plurality of variable parameters simultaneously by simultaneously changing variables such as line width and thickness of the target grating.

Figure 1:
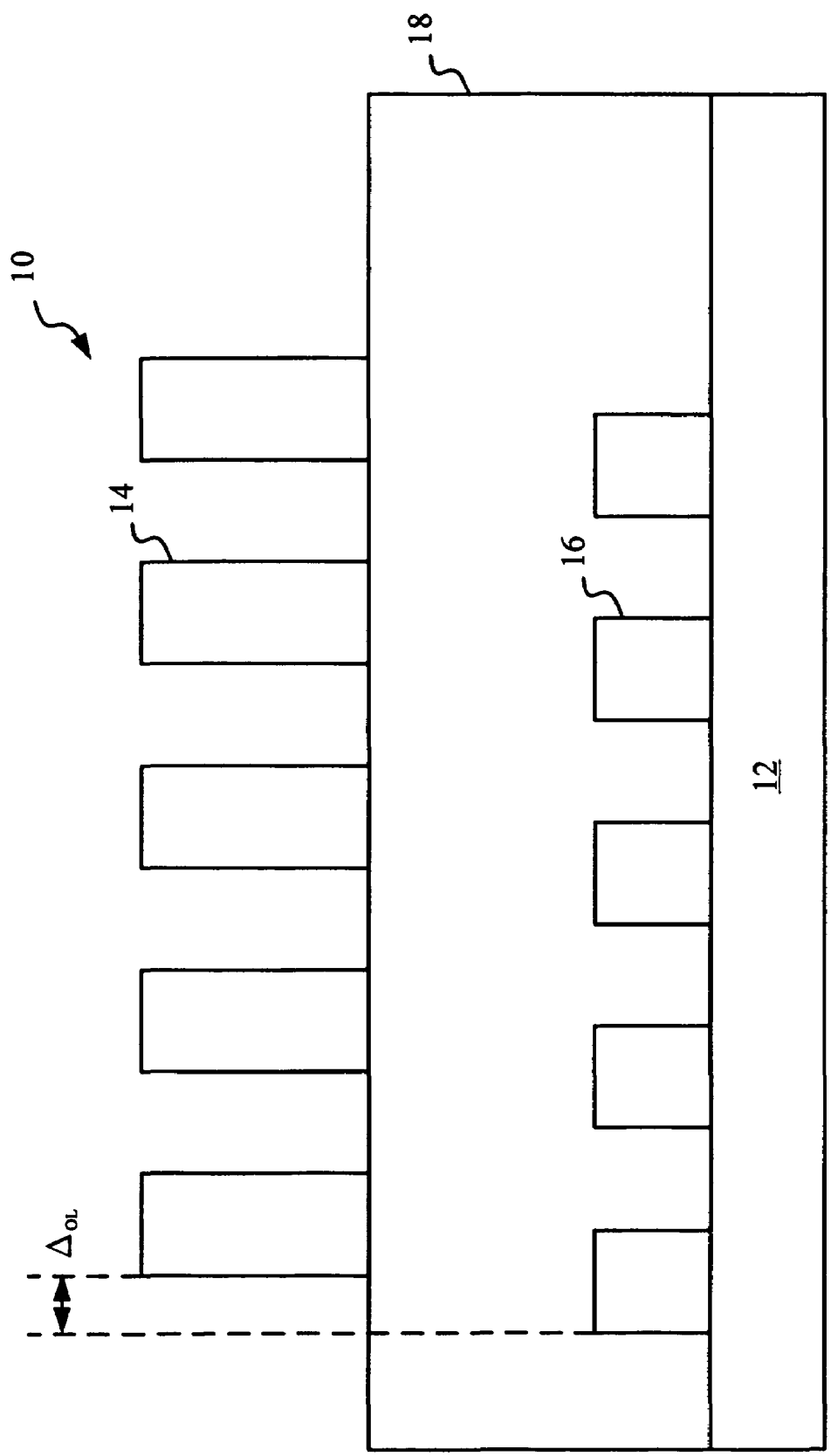
FIG. 1 illustrates an overlay mark.

FIG. 1 illustrates an example of an overlay mark 10. The overlay mark 10 has a first grating 14 made of photoresist on an intermediate layer 18 made of polysilicon, and a second grating 16 made of silicon dioxide on a bottom layer 12 made of silicon. The pitch of the first grating 14 is the same as that of the second grating 16, and $\Delta_{OL}$ represents the overlay error between these two gratings 14 and 16. In this example, the thickness, refractive index and extinction coefficient of these layers are summarized in the following table:

|  | Material | Thickness | Refractive index | Extinction coefficient |
| --- | --- | --- | --- | --- |
| First grating | Photoresist | 7671.8 Å | 1.62399 | 0 |
| Intermediate layer | Polysilicon | 1970.6 Å | 3.925959 | 0.0594 |
| Second grating | Silicon dioxide | 494 Å | 1.462589 | 0 |
| Bottom layer | Silicon | — | 3.866894 | 0.019521 |

The measuring sensitivity for the overlay error of the overlay mark 10 is affected not only by the mechanical design of the measuring machine, the backend detector and the signal processing technique, but also by the structural parameters of the overlay mark 10, which influences the shape of the diffraction spectrums (signatures) and the separating degree between these diffraction signatures. For example, structural parameters such as refractive index, extinction coefficient, thickness, geometric figure and sidewall angle after etching processes, all influence the measuring sensitivity for the overlay error of the overlay mark 10.

Figure 2:
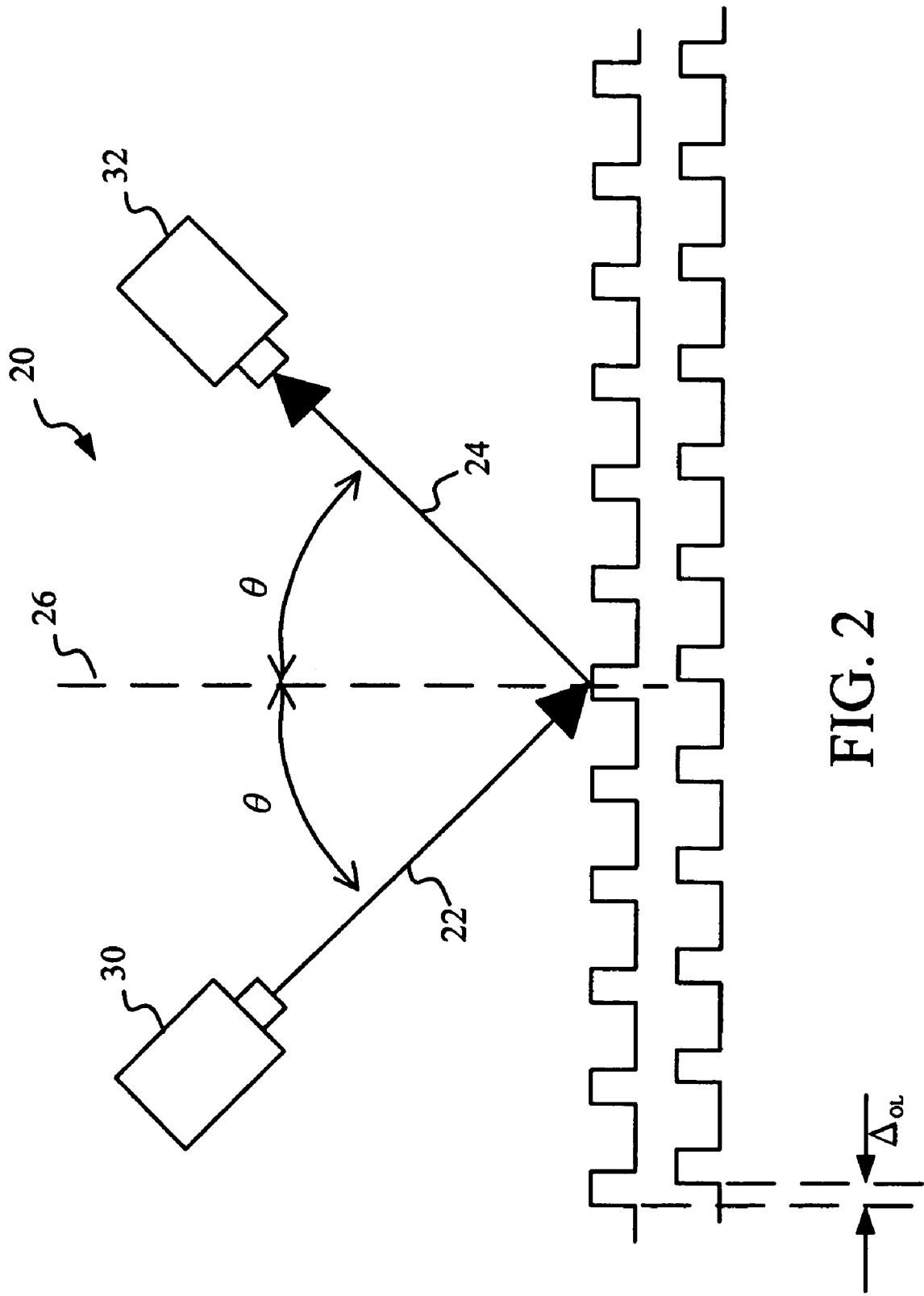
FIG. 2 illustrates the system architecture of an angular scatterometer.

FIG. 2 illustrates an angular scatterometer 20. Although an angular scatterometer 20 is shown and described here, spectroscopic reflectometers and specular spectroscopic ellipsometers may equivalently be used. The angular scatterometer 20 uses a single wavelength laser and scans at multiple incident angles. The included angle between a normal line 26 and an incident beam 22 from a light source 30 is the same as that between the normal line 26 and a diffraction beam. The detector 32 only detects the zero-order diffraction beam. The incident beam 22 can use currently available lasers such as argon-ion laser (488 nanometers and 514 nanometers), HeCd laser (442 nanometers), HeNe laser (612 nanometers and 633 nanometers) and Nd:YAG (532 nanometers), or others. A diffraction signature between the incident beam 22 and the diffraction beam 24 can be acquired by changing the incident angle θ.

Figure 3:
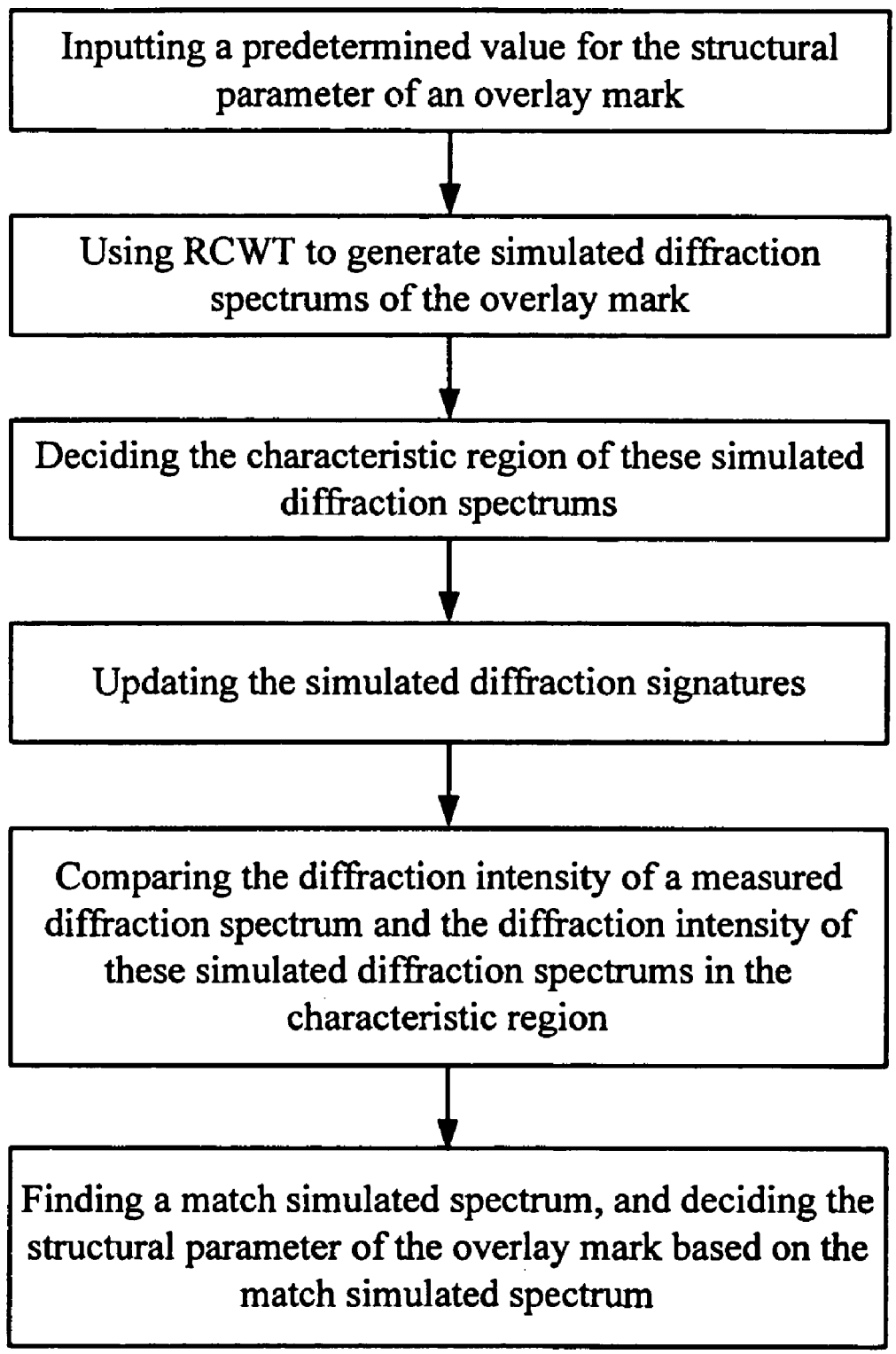
FIG. 3 illustrates a flow chart for deciding structural parameters of an overlay mark according to one embodiment of the present invention.

FIG. 3 illustrates a flow chart for deciding structural parameters of the overlay mark 10. After inputting a predetermined value (a guessed value) for structural parameters such as the overlay error of the overlay mark 10, a rigorous coupled wave theory (RCWT) algorithm is used to build a diffraction library including a plurality of simulated diffraction spectrums. For example, based on a guessed value of 200 nm, an RCWT algorithm is used to generate five simulated diffraction spectrums 150, 175, 200, 225 and 250 nanometers.

Subsequently, a portion of the incident angles is selected as a characteristic region based on the root mean square error of these simulated diffraction spectrums. Particularly, the characteristic region of the plurality of simulated diffraction spectrums is an incident angle region, and these simulated diffraction spectrums have a root mean square error larger than the noise level of a measuring machine. Consequently, the diffraction intensity of a measured diffraction spectrum is compared with the diffraction intensity of these simulated diffraction spectrums in the characteristic region to find a match spectrum. The structural parameter of the overlay mark 10 is determined based on the match spectrum. After the characteristic region of these simulated diffraction spectrums is selected, the diffraction data in the characteristic region can be used to replace these diffraction data in the entire incident angles in the diffraction library to reduce the required storage capacity.

Figure 4A:
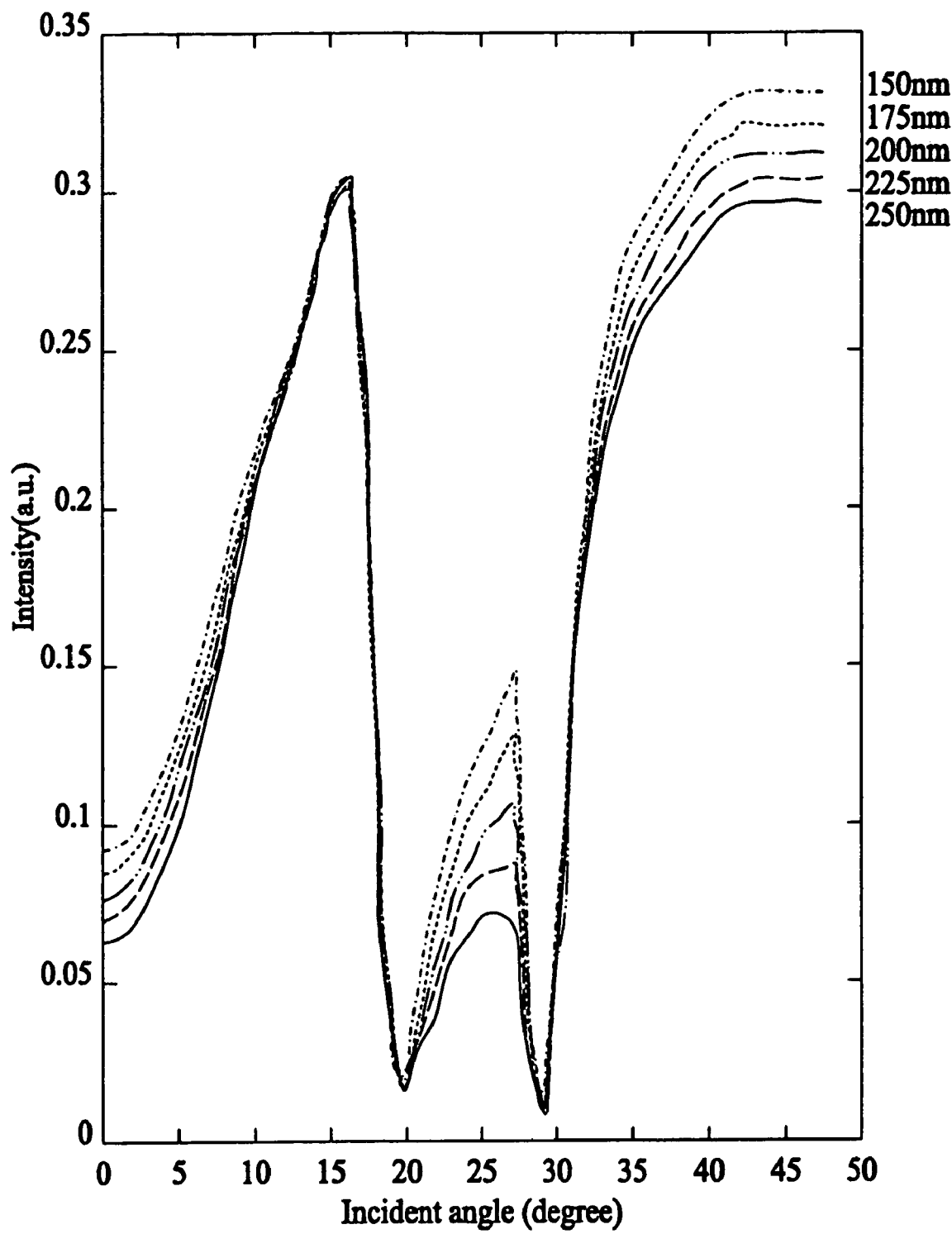
FIG. 4(a) and FIG. 4(b) illustrate a diffraction library according to one embodiment of the present invention.
Figure 4B:
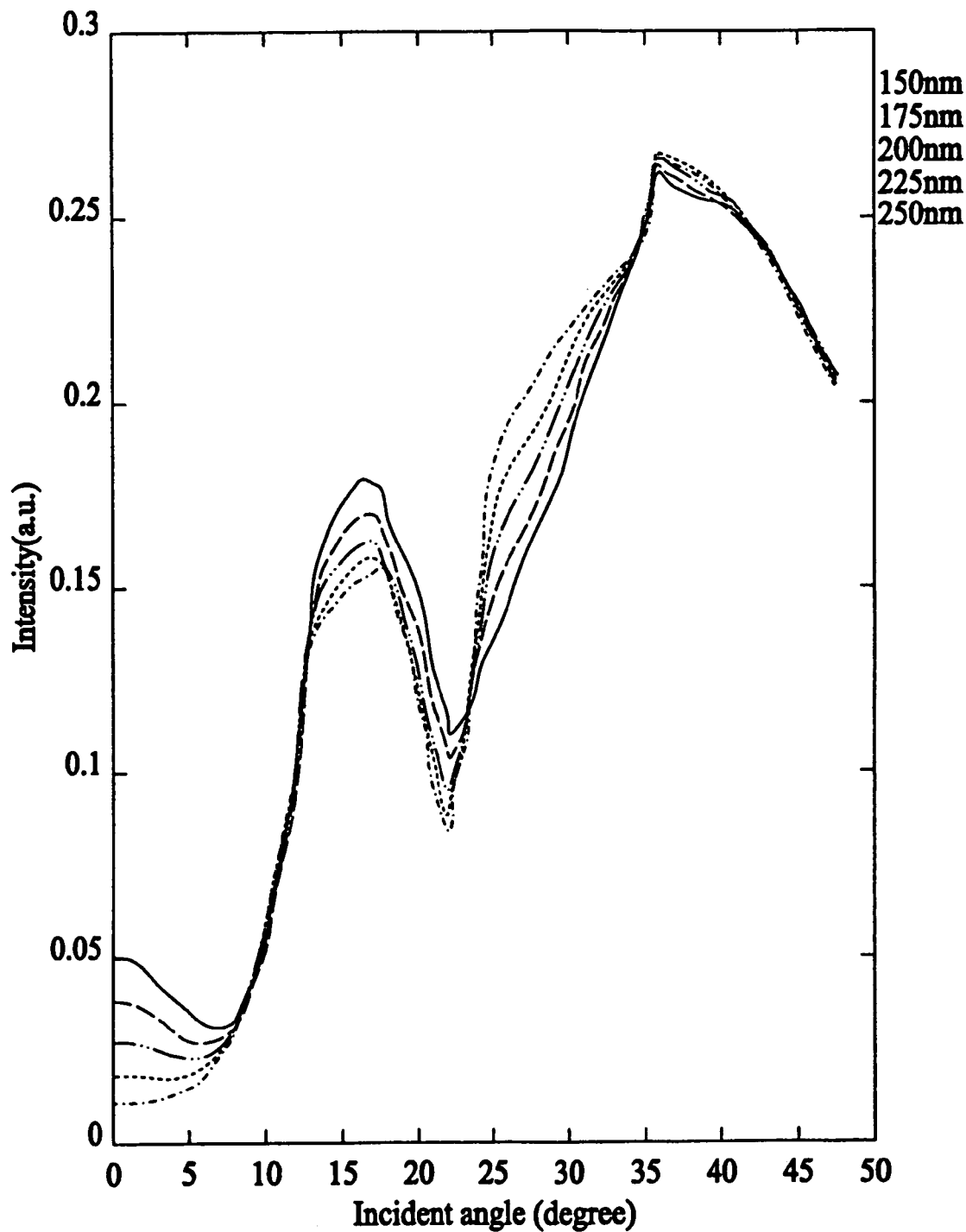

FIG. 4(a) and FIG. 4(b) illustrate one example of a diffraction library, wherein the overlay error of these five simulated diffraction spectrums is 150, 175, 200, 225 and 250 nanometers, for s-polarization and p-polarization, respectively. Rigorous coupled wave theory may be used to build the diffraction library according to a predetermined structural parameter such as overlay error, critical dimension, pitch, thickness and line-to-space ratio.

The s-polarization beam possesses a larger variation of diffraction intensity in a certain incident angle region rather than a linear variation of diffraction intensity for all incident angles, while the other incident angle region possesses a smaller variation of diffraction intensity, as shown in FIG. 4(a). Similarly, the p-polarization beam possesses the same property, as shown in FIG. 4(b). After the diffraction library is built, the present method proceeds to select the characteristic region of these simulated diffraction spectrums in the diffraction library. The separating degree of the plurality of simulated diffraction spectrums of the s-polarization beam at incident angles between 22 and 27 degrees is larger than at other incident angles, i.e., these simulated diffraction spectrums possess higher resolutions at incident angles between 22 and 27 degrees. In other words, in this example, the incident angle region between 22 and 27 degrees can be regarded as the characteristic region of these simulated diffraction spectrums.

Figures 5A, 5B:
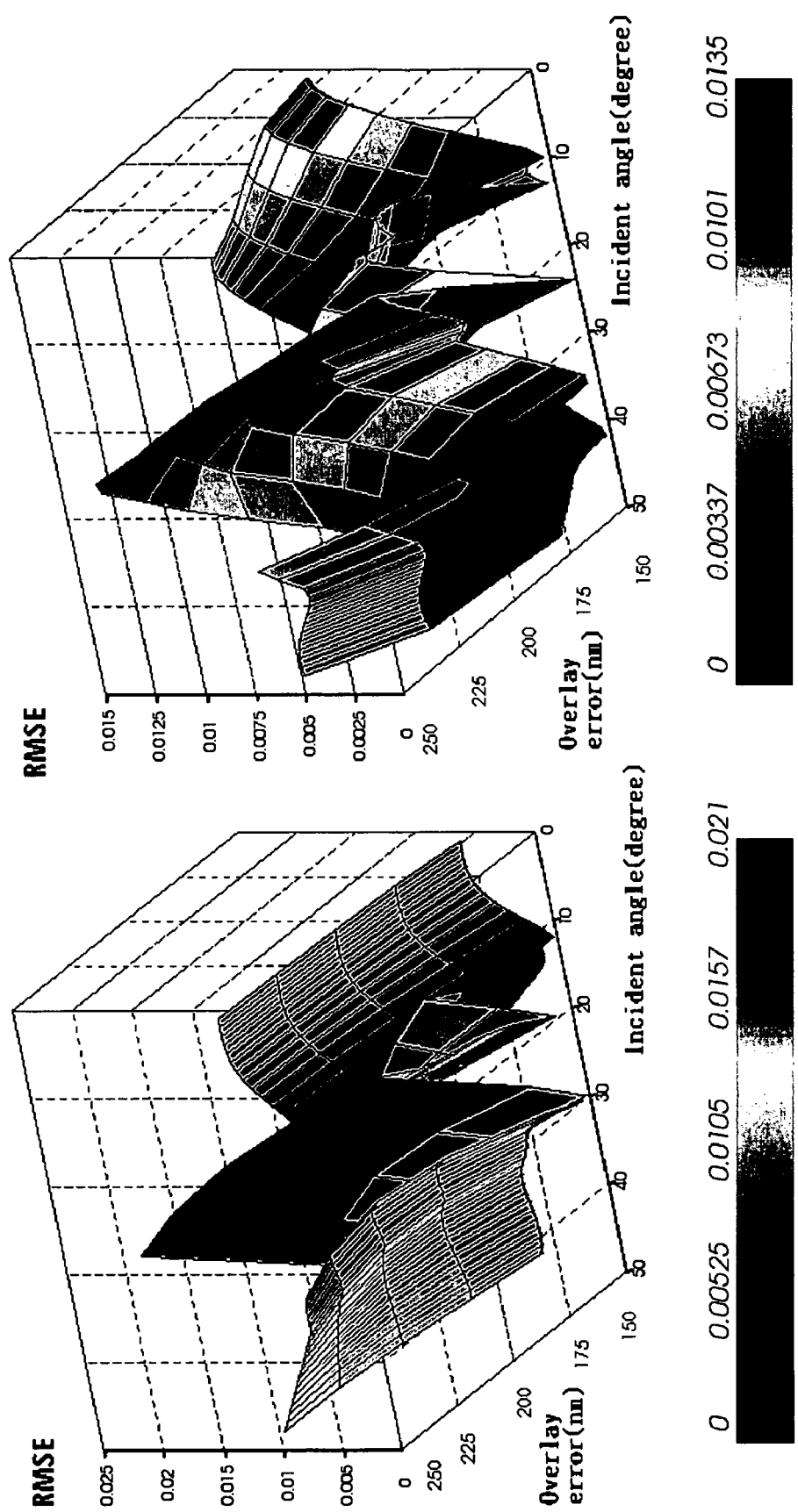
FIG. 5(a) illustrates the relationship of RMSE and overlay error to the incident angle of the s-polarization beam.
FIG. 5(b) illustrates the relationship of RMSE and overlay error to the incident angle of the p-polarization beam.

FIG. 5(a) illustrates the relationship of RMSE and overlay error to the incident angle of the s-polarization beam, and FIG. 5(b) illustrates the relationship of RMSE and overlay error to the incident angle of the p-polarization beam. The present method optionally uses the RMSE to quantify the separating degree of these simulated diffraction spectrums, and selects the characteristic region of these simulated diffraction spectrums based on a criteria if RMSE is larger than a noise level of a measuring machine. RMSE is defined as below:

$$RMSE = \sqrt{\frac{\sum_{i=1}^{N}(x_i - y_i)^2}{N}}$$

wherein x and y represents the diffraction intensity of two simulated diffraction spectrums, respectively, and N represent the sampling count of each simulated diffraction spectrum. As shown in the drawings, s-polarization beams and p-polarization beams possess a larger RMSE at incident angles between 20 and 30 degrees.

Figure 6:
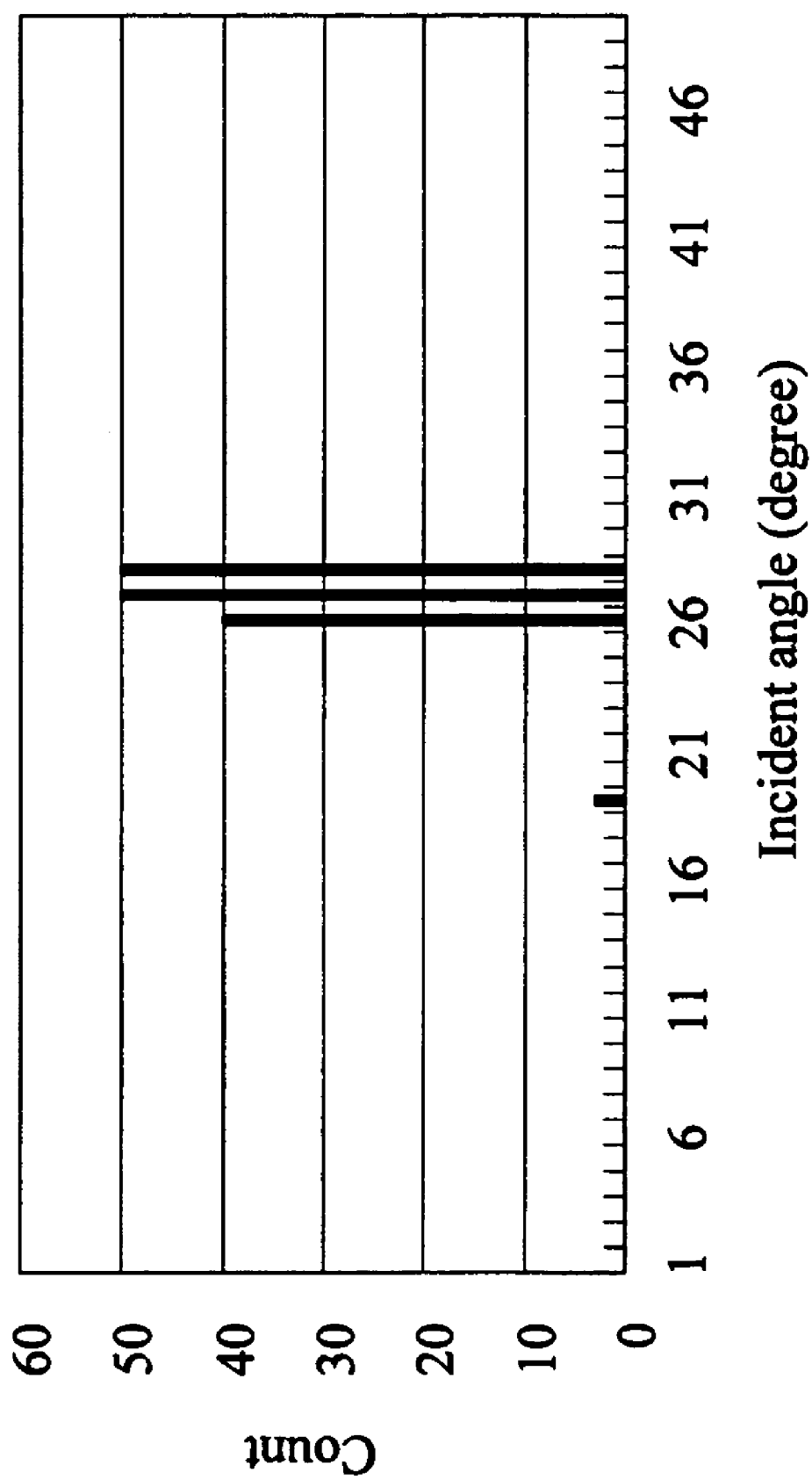
FIG. 6 is a static diagram showing the sampling count of the RMSE larger than the noise level of a measuring machine.

FIG. 6 is a static diagram showing the sampling count of RMSE larger than the noise level of the measuring machine, wherein the noise level is set to be 0.001. For the overlay error between 150 and 250 nanometers, RMSE of all the s-polarization beams are larger than the noise level of the measuring machine as the incident angle is between 26 and 29 degrees. Consequently, the incident angle region between 26 and 29 degrees of the s-polarization beam can be regarded as the characteristic region if the overlay error between the first grating 14 and the second grating 16 is in a range between 150 and 250 nanometers.

Figure 7A:
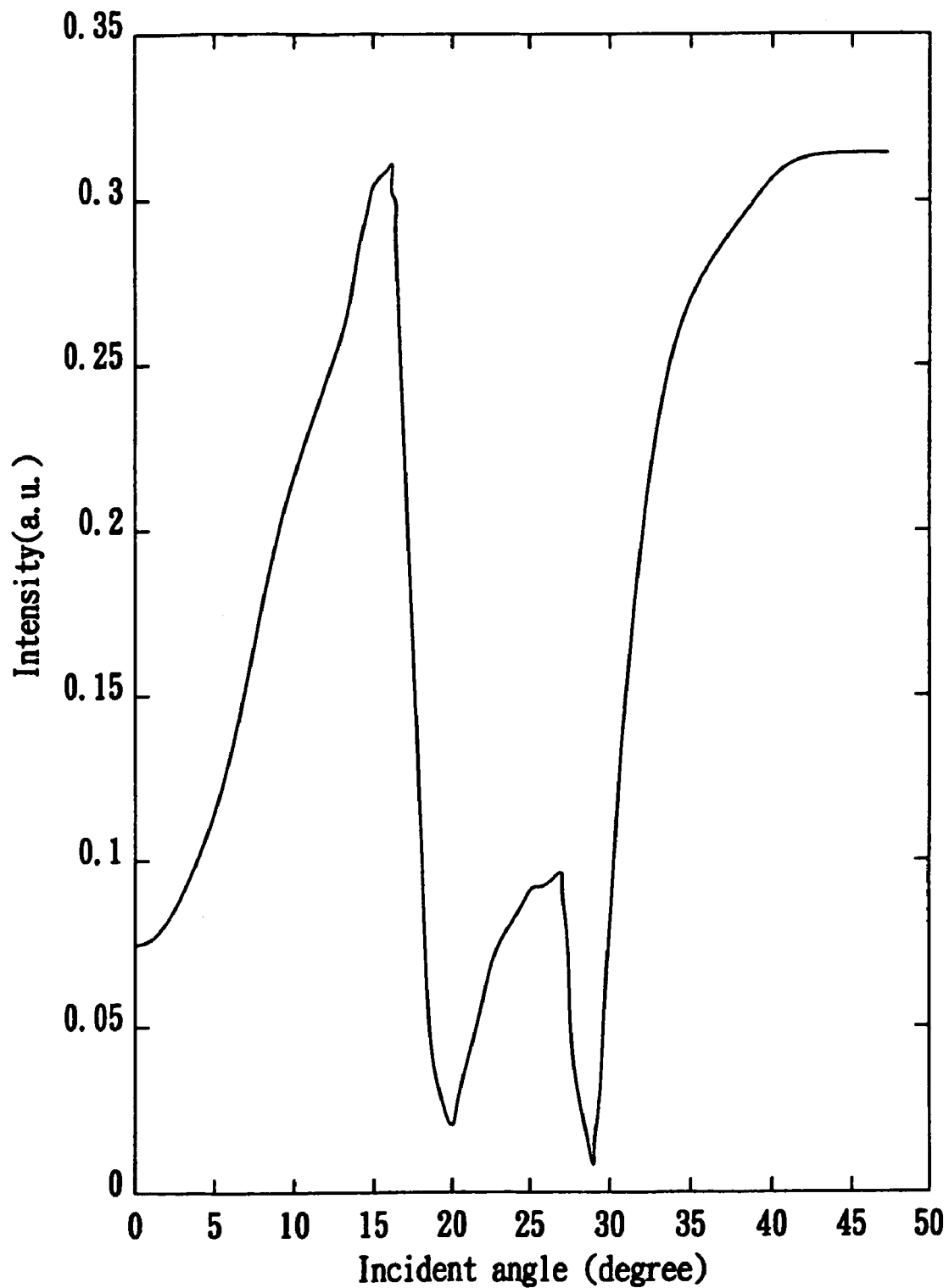
FIG. 7(a) and FIG. 7(b) illustrate the s-polarization diffraction spectrum and the p-polarization spectrum from a measuring machine.
Figure 7B:
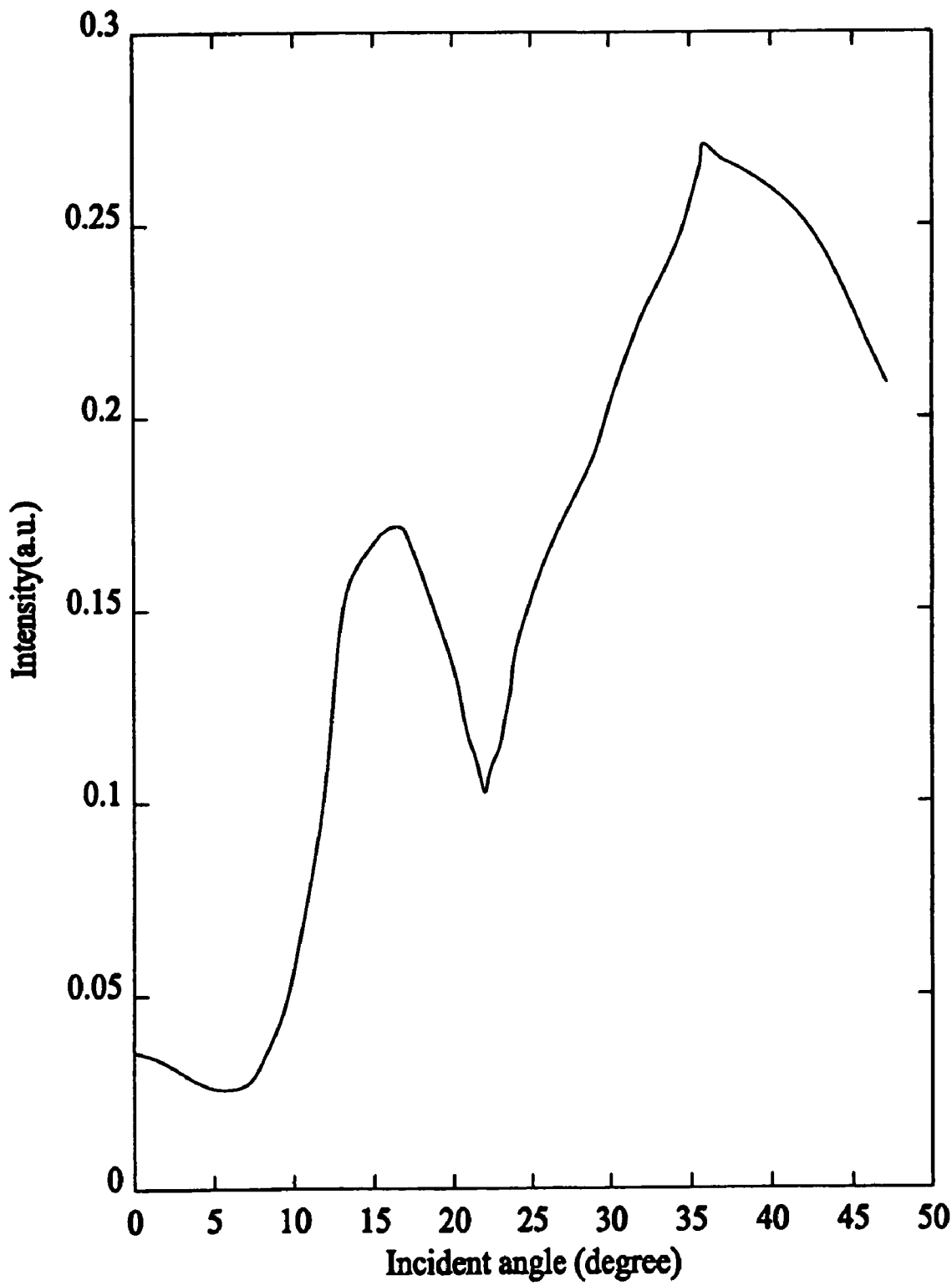

FIG. 7(a) and FIG. 7(b) illustrate the s-polarization diffraction spectrum and the p-polarization spectrum from a measuring machine, respectively. After selecting the characteristic region, the present method proceeds to compare the diffraction intensity of the measured diffraction spectrum with that of these simulated diffraction spectrums in the characteristic region to find a match simulated diffraction spectrum, i.e., the diffraction intensity of the s-polarization diffraction spectrum at the incident angles between 26 and 29 degrees in FIG. 7(a) is compared with that of these five simulated diffraction spectrums at the incident angles between 26 and 29 degrees in FIG. 4(a) to find the match spectrum. Consequently, the structural parameter of the overlay mark 10 is decided based on the match spectrum.

Figure 8:
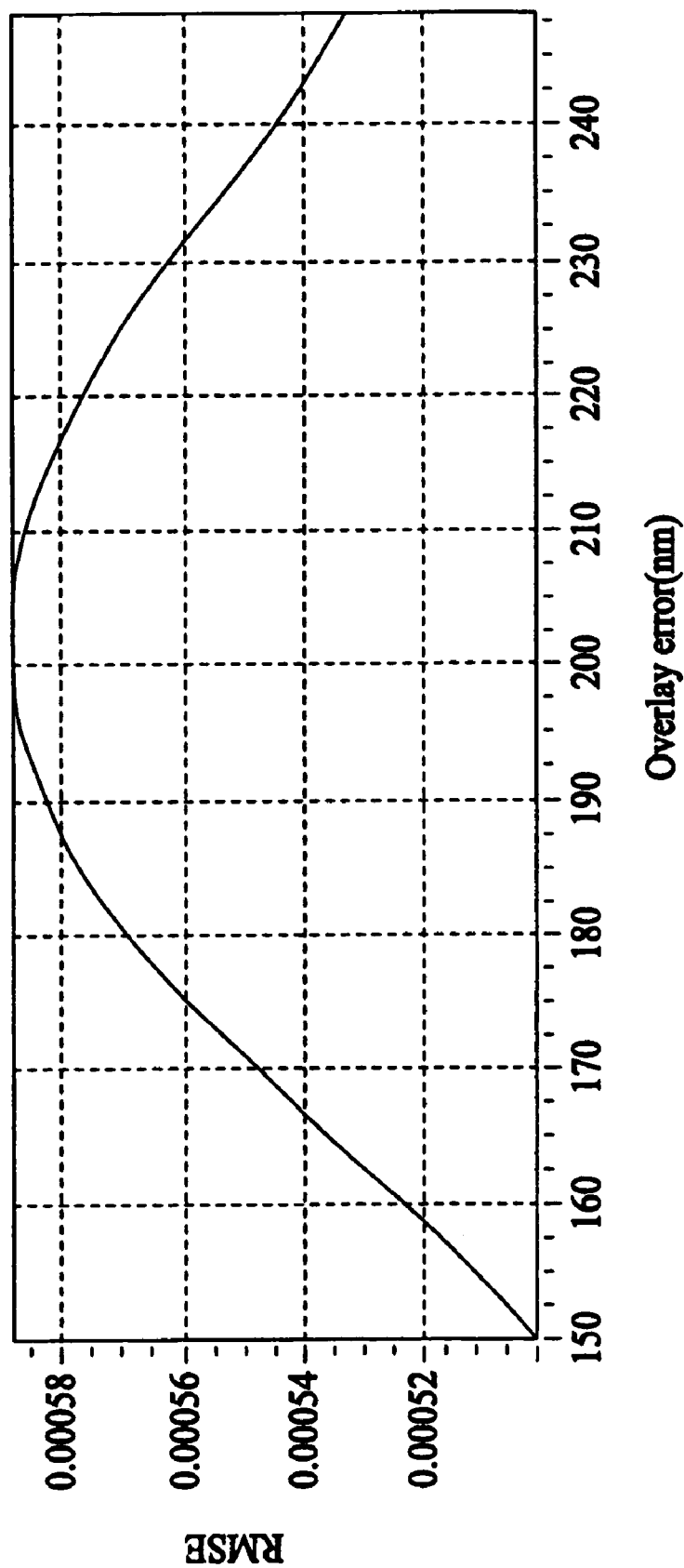
FIG. 8 illustrates the average RMSE of the s-polarization beam and the p-polarization beam at the incident angle between 0 and 47 degrees.
Figure 9:
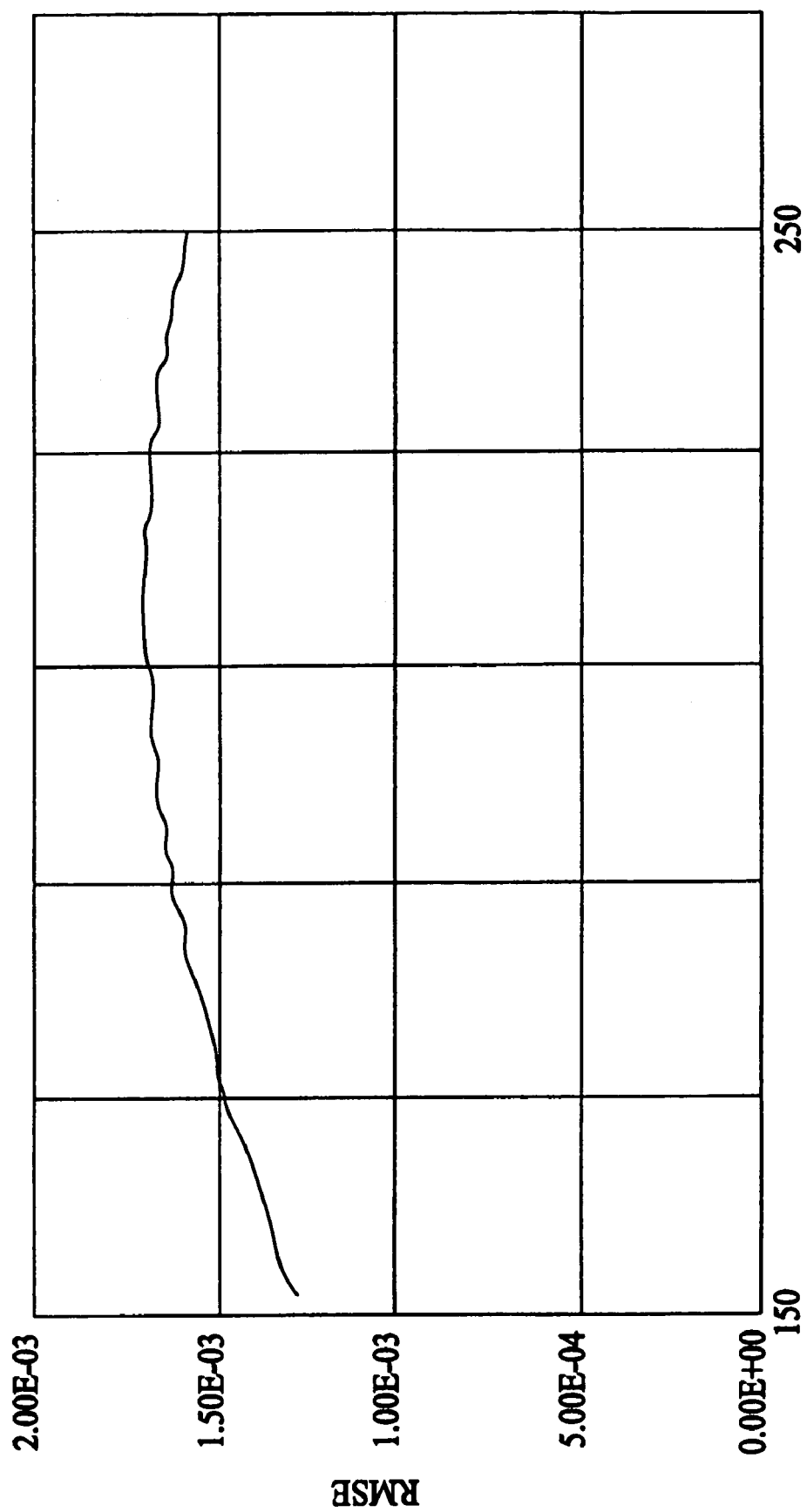
FIG. 9 illustrates the RMSE of the s-polarization beam at the incident angle of 28 degrees.

FIG. 8 illustrates the average RMSE of the s-polarization beam and the p-polarization beam at the incident angle between 0 and 47 degrees, and FIG. 9 illustrates RMSE of the s-polarization beam at the incident angle of 28 degree. As shown in FIG. 8, the largest RMSE about 0.000589 occurs at the overlay error of 200 nanometers, i.e., the conventional comparison of the entire diffraction spectrum can achieve the largest RMSE about 0.000589. In contrast, the present method can select the incident angle of 28 degree as the characteristic incident angle, and its corresponding RMSE at the overlay error of 200 nanometers is about 0.001649, i.e., about 2.8 times of the largest RMSE for the conventional technique of comparing the entire diffraction spectrum. In other words, using the incident angle of 28 as the characteristic incident angle of the diffraction spectrum to represent the entire measured diffraction spectrum, the present method can increase the measurement precision by 2.8 times without changing the hardware measuring machine.

In summary, a method for efficiently and accurately determining grating profiles uses characteristic signature matching in a discrepancy enhanced library generation process. Using light scattering theory, a series of scattering signatures vs. scattering angles or wavelengths are generated based on the designed grating parameters, eg. CD, thickness and Line:Space ratio. This method selects characteristic portions of the signatures wherever their discrepancy exceeds the preset criteria and reforms a characteristic signature library for quick and accurate matching.

The invention claimed is:

1. A scatterometry method, comprising:
    entering grating structure parameters into a computer;
    calculating a diffraction profile based on the grating structure parameters over a first range of incident light values;
    incrementally changing one or more of the grating structure parameters;
    repeatedly calculating a diffraction profile and incrementally changing one or more of the grating structure parameters to calculate additional diffraction profiles based on the changed grating structure parameters over the first range of incident light values;
    identifying a characteristic region of the calculated diffraction profiles wherein a change in an incrementally increasing grating structure parameter value causes a change exceeding a threshold value among the diffraction profiles;
    storing the characteristic regions of the calculated diffraction profiles in a library;
    performing scatterometry on a sample substrate and generating scattering signatures over a second range of incident light values;
    comparing the scattering signatures with the calculated diffraction profiles in the library; and
    identifying a calculated diffraction profile that matches the scattering signature to a selected level of similarity.

2. The method of claim 1 wherein the incident light values in the first range and the second range are incident light angles.

3. The method of claim 1 wherein the incident light values in the first range and the second range are incident light polarization types.

4. The of the method claim 1 wherein the calculated diffraction profile with the characteristic region that most closely matches a corresponding characteristic region of the scattering signature is identified.

5. The method of claim 1 wherein the grating structure parameters are parameters of a semiconductor substrate having two or more layers with a grating structure on two or more layers.

6. The method of claim 5 wherein the grating structure parameters include one or more of grating line width, grating line to space ratio, grating overlay offset; film thickness of each layer, optical properties of each layer; and shape characteristics of each layer.

7. The method of claim 1 wherein only the characteristic regions of the calculated diffraction profiles are stored in the library.

8. A method for performing scatterometry on a substrate, comprising:
    entering grating structure parameters and substrate parameters into a computer;
    calculating a diffraction profile based on the grating structure and substrate parameters over a first range of incident light angles;
    incrementally increasing the grating overlay offset between gratings on different layers;
    repeatedly calculating a diffraction profile and incrementally changing one or more of the grating structure parameters to calculate additional diffraction profiles based on the changed grating overlay offset;

identifying a characteristic region of the calculated diffraction profiles wherein an incremental change in a overlay parameter step causes the most change between calculated diffraction profiles, over the first range of incident light angles;

storing only the characteristic regions of the calculated diffraction profiles in a library;

performing scatterometry on the substrate and measuring scattering signatures over a second range of incident light angles;

comparing scattering only the measured signatures with characteristic region of the calculated diffraction profiles in the library;

identifying the calculated diffraction profile that most closely matches with the measured scattering signature;

determining the overlay offset based on the overlay offset of the calculated diffraction profile matching the measured scattering signature.

9. A scatterometry system, comprising:

an incident light source;

means for changing a value of the incident light source;

a light detector;

a computer linked to the incident light source and to the light detector, with the computer having:

means for calculating a diffraction profile based on grating structure parameters over a range of incident light values;

means for incrementally changing one or more of the grating structure parameters;

means for re-calculating additional diffraction profiles based on the changed grating structure parameters over the range of incident light values;

means for identifying a characteristic region of the calculated diffraction profiles wherein a change in a grating structure parameter value causes a change exceeding a threshold value among the diffraction profiles;

means for storing the characteristic regions of the calculated diffraction profiles in a look up table;

means for comparing the scattering signatures with the calculated diffraction profiles in the library; and means for identifying a calculated diffraction profile that matches with the scattering signature to a selected level of similarity.

10. The method of claim 1 wherein the first range of incident light values is the same as the second range of incident light values.

11. The method of claim 1 wherein the incident light values in the first range and the second range are incident light wavelengths.

12. The method of claim 8 wherein the first range of incident light values is the same as the second range of incident light values.

13. The method of claim 8, wherein the grating structure parameters include at least one of line width, and line:space ratio and wherein the substrate parameters include at least one of film thickness, optical properties of each layer on the substrate, shape information and pattern information.

14. A method comprising:

calculating a scatter signature based on a structure parameters of a feature on a sample over a first range of incident light values;

incrementally changing one or more of the structure parameters;

repeatedly calculating additional scatter signatures and incrementally changing one or more the structure parameters to produce a plurality of calculated scatter signatures;

identifying a characteristic region of the plurality of calculated scatter signatures, the characteristic region being a region in the plurality of calculated scatter signatures that is more sensitive to changes in the structure parameters than other regions in the plurality of calculated scatter signatures; and storing the characteristic regions of the plurality of calculated scatter signatures in a library.

15. The method of claim 14 wherein the characteristic region is identified by a change in the calculated scatter signatures caused by the incrementally increasing structure parameter value exceeding a threshold value.

16. The method of claim 14 wherein the incident light values in the first range are at least one of incident light angles, incident light polarization types, and incident light wavelengths.

17. The method of claim 14, wherein identifying a characteristic region of the plurality of calculated scatter signatures comprises identifying a region in the plurality of calculated scatter signatures in which the changing one or more of the structure parameters causes a change in the calculated scatter signature that exceeds a threshold value.

18. The method of claim 17, wherein determining a change in the calculated scatter signature that exceeds a threshold value is performed using a root mean square error.

19. The method of claim 17, wherein the threshold value is a noise level of a metrology system with which the library is used.

20. The method of claim 14, wherein the structure parameters are parameters of a semiconductor substrate having two or more layers with a grating structure on two or more layers and include at least one of grating line width, grating line to space ratio, grating overlay offset; film thickness of each layer, optical properties of each layer; and shape characteristics of each layer.

21. The method of claim 14, wherein regions outside the characteristic regions of the plurality of calculated diffraction profiles are not stored in the library.

22. The method of claim 14, further comprising:

performing scatterometry on a sample and generating an experimental signature over a second range of incident light values, the experimental signature having a characteristic region that corresponds to the characteristic region of the plurality of calculated scatter signatures;

comparing the characteristic regions of the experimental signature with the characteristic region of the plurality of calculated scatter signatures; and identifying a matching calculated scatter signature having a characteristic region that matches the characteristic region of the experimental signature to a selected level of similarity; and determining the structure parameters based on the matching calculated scatter signature.

23. The method of claim 22 wherein the first range of incident light values is the same as the second range of incident light values.

24. The method of claim 22, wherein identifying a matching calculated scatter signature is performed using at least one of root mean square error, means square error and square distance.

* * * * *

UNITED STATES PATENT AND TRADEMARK OFFICE
CERTIFICATE OF CORRECTION

PATENT NO.        : 7,532,317 B2                                     Page 1 of 1
APPLICATION NO. : 11/319677
DATED             : May 12, 2009
INVENTOR(S)       : Nigel Smith et al.

It is certified that error appears in the above-identified patent and that said Letters Patent is hereby corrected as shown below:

<u>Claim 4</u>:

At Column 6, line 38, please delete "The of the method" and insert --The method--.

<u>Claim 8</u>:

At Column 8, line 11, please delete "comparing scattering only the measured signatures with characteristic region of the calculated diffraction profiles in the library" and insert --comparing the measured scattering signatures only with the characteristic region of the calculated diffraction profiles in the library--.

Signed and Sealed this

Fourteenth Day of July, 2009

JOHN DOLL
*Acting Director of the United States Patent and Trademark Office*